United States Patent [19]

Surmatis

[11] B 3,989,757

[45] Nov. 2, 1976

[54] ISOMERIZING CIS-CAROTENOIDS TO ALL-TRANS-CAROTENOIDS

[75] Inventor: Joseph Donald Surmatis, West Caldwell, N.J.

[73] Assignee: Hoffmann-La Roche Inc., Nutley, N.J.

[22] Filed: Apr. 29, 1974

[21] Appl. No.: 465,202

[44] Published under the second Trial Voluntary Protest Program on February 24, 1976 as document No. B 465,202.

Related U.S. Application Data

[63] Continuation-in-part of Ser. No. 392,597, Aug. 29, 1973, abandoned.

[52] U.S. Cl. .......................... 260/598; 260/666 C; 260/617 B; 260/514 L; 260/642 R; 260/348 C; 260/346.2 R; 260/635 R; 260/683.2; 260/537 N; 260/586 R; 260/594

[51] Int. Cl.$^2$.......................................... C07C 45/00

[58] Field of Search ................ 260/598, 666 C, 666, 260/617 B, 514 A, 642, 348 C, 346.2 R, 635 R, 683.2, 537 N, 586 R, 594, 514 L

[56] References Cited

UNITED STATES PATENTS 3,441,623   4/1969   Surmatis ............................ 260/666

OTHER PUBLICATIONS

Eliel, Stereochemistry of Carbon Compounds, (1962), 341–342.

*Primary Examiner*—Bernard Helfin
*Attorney, Agent, or Firm*—Samuel L. Welt; Bernard S. Leon; Richard A. Gaither

[57] ABSTRACT

Cis-isomers of a carotenoid are isomerized to an all-trans-isomer of the carotenoid by heating the cis-isomers in water at above about 50° C.

8 Claims, No Drawings

ISOMERIZING CIS-CAROTENOIDS TO ALL-TRANS-CAROTENOIDS

CROSS REFERENCE TO RELATED APPLICATIONS

This application is a continuation-in-part of patent application Ser. No. 392,597, filed Aug. 29, 1973 now abandoned, entitled "Isomerizing Cis-Carotenoids To All Trans-Carotenoids".

BACKGROUND OF THE INVENTION

In the synthesis of various carotenoids, mixtures of cis- and trans-isomers are typically produced. In general, the all-trans-isomer of a carotenoid is much more valuable than any of the cis-isomers, and, for many carotenoids, the all-trans-isomer is the only isomer of any commercial value. For this reason, with respect to a large number of carotenoids, ways have been sought to convert cis-isomers to the corresponding all-trans-isomer.

The methods found for converting cis-carotenoids to all-trans-carotenoids have not been entirely satisfactory. See for example U.S. Pat. No. 2,849,507 and U.S. Pat. No. 3,441,623. Note also Karrer and Jucker, Carotenoids, Elsevier Publ. Co., Inc., Amsterdam, pp. 38–42 (1950) and Helv. Chim. Acta., 39, 249 (1956). In U.S. Pat. Nos. 2,849,507 and 3,441,623, cis-$\beta$-carotene is converted to all-trans-$\beta$-carotene by heating the cis-isomer in an inert organic liquid. However, the all-trans-$\beta$-carotene obtained by the processes of these patents invariably contains at least a small amount of cis-isomers as contaminants. The residual cis-isomers are difficult to remove and render the $\beta$-carotene obtained unsatisfactory for human consumption unless removed.

There has been an unfilled need, therefore, for a generally applicable method for completely converting cis-isomers of a carotenoid to the corresponding all-trans-isomer without the need for carrying out extensive purification procedures to removal residual cis-isomers.

SUMMARY OF THE INVENTION

In accordance with this invention, a process is provided for converting a cis-isomer of a carotenoid to an all-trans-isomer of the carotenoid by heating the cis-isomer in water to a temperature above about 50°C. By the process of this invention, cis-isomers of a carotenoid can be converted to the corresponding all-trans-isomer, substantially free of cis-isomers, without the need for carrying out further process steps to remove residual cis-isomers.

DETAILED DESCRIPTION OF THE INVENTION

In accordance with the process of this invention, a cis-isomer of a carotenoid can be converted to the corresponding all-trans-isomer of the carotenoid by heating the cis-isomer in water to a temperature above about 50°C.

As used throughout this application, the term "cis-isomer of a carotenoid" or "cis-isomer" comprehends an isomer of a carotenoid having at least one bond which is cis. Included within the term "cis-isomer of a carotenoid" or "cis-isomer" are mixtures containing more than one cis-isomer of the carotenoid and which may also contain the corresponding all-trans-isomer of the carotenoid. As also used throughout this application, the term "all-trans-isomer of the carotenoid" or "all-trans-isomer" comprehends the isomer of the carotenoid having no cis-bond.

As used throughout this application, the term "carotenoid" or "carotenoids" comprehends the class of pigments containing a plurality of conjugated double bonds, across which cis and trans isomerism can occur. Among the carotenoids which can be isomerized from cis- to all-trans in accordance with this application are the $C_{30}$ to $C_{50}$ carotenoids, such as: the carotenoid hydrocarbons, particularly:

Lycopene,
Prolycopene,
$\beta$-Carotene,
$\gamma$-Carotene,
$\alpha$-Carotene, and
Pro-$\gamma$-carotene;

the carotenoids containing hydroxyl groups, particularly:

Lycoxanthin,
Rubixanthin,
Cryptoxanthin,
Zeaxanthin,
Antheraxanthin,
Violaxanthin,
Auroxanthin,
Xanthophyll,
Flavoxanthin,
Chrysanthemaxanthin, and
Lycophyll;

the carotenoids containing one or more carbonyl groups, particularly:

Canthaxanthin,
$\beta$-Citraurin,
Rhodoxanthin,
Myxoxanthin,
Myxoxanthophyll,
Astacene and Astaxanthin,
Capsanthin,
Capsorubin,
$\beta$-Apo-8'-carotenal, and
$\beta$-Apo-11'-carotenal; and the carotenoid carboxylic acids, particularly:

Bixin,
Crocetin, and
Axafrin.

In accordance with this invention, water provides several additional advantages in isomerizing carotenoids, besides providing an all-trans-isomer substantially free of cis-isomers. Because all carotenoids are substantially insoluble in it, water is suitable for isomerizing virtually all carotenoids. Also, because water is a safe and simple medium to use, in that it is non-flammable and its vapors are not deleterious to humans, and because it is cheap, the use of water provides a technically and economically attractive method of isomerization.

In carrying out the isomerization of this invention, the cis-isomer of a carotenoid can be converted to the all-trans-isomer of the carotenoid merely by adding the cis-isomer to water and heating the aqueous mixture to a temperature above about 50°C. In carrying out this procedure, the relative amounts of cis-isomer and of water are not critical. However, it is preferred that sufficient water be utilized so that the cis-isomer is completely immersed in the water during heating.

Also in carrying out this isomerization, particular temperatures and pressures are not critical. In this process, any temperature between about 50°C. and the degradation temperature of the cis-carotenoid utilized and atmospheric pressure can be utilized conveniently. Preferably, temperatures of about 50°C. to 120°C. are utilized, especially temperatures of about 70°C. to about 100°C., particularly temperatures of about 100°C.

Further in carrying out this isomerization procedure, the time of heating is not critical. Preferably, heating of the cis-isomer is carried out until analysis of the carotenoid shows only the all-trans-isomer to be present. 20 hours is usually sufficient to complete isomerization of the cis-isomers to the corresponding all-trans-isomer.

If desired, the aqueous carotenoid mixture can be stirred during isomerization. Preferably, the mixture is caused to agitate itself by heating the mixture to its boiling point.

The all-trans carotenoid formed by the isomerization process of this application can be isolated in a conventional manner, such as by filtration. The all-trans-isomer is obtained in purities of up to 100% by the procedure of this application. As a result, no additional processing is required to isolate the all-trans-isomer, free of cis-isomers.

The examples which follow further illustrate the process of this application.

EXAMPLE 1

The Isomerization of β-apo-8'-carotenal 500 g. of crude apo-8'-carotenal, containing about equal parts of cis-isomers and the all-trans isomer along with other $C_{30}$ polyene compounds (about 75% by weight apo-8'-carotenal content), produced in accordance with Ruegg et al., Helv. Chim. Acta., 42, 854 (1959), was placed in a 12-liter flask with 8 liters of water. The contents of the flask were stirred at the boiling temperature of the water for 72 hours, until ultraviolet analysis and thin layer chromatography showed that substantially all the cis-isomers had been converted to the all-trans isomer. The flask then was cooled in a water bath and the product was filtered, washed with 2 liters of methyl alcohol, and dried under vacuum at 60°C. There was obtained 471.8 g. of crude, dry, all-trans-β-apo-8'-carotenal, with an ultraviolet spectrum showing a single peak at 459 mμ (cyclohexane). The absence of a second u.v. peak at 320 mμ showed that the material contained no cis-β-apo-8'-carotenal; m.p. 128°–130°C. The dry all-trans-β-apo-8'-carotenal was dissolved in 2 liters of methylene chloride by stirring at room temperature 22°C., and it was filtered through filter aid. The solution was diluted with 4 liters of methyl alcohol and cooled overnight at +10°C. The crystallized product was filtered, washed with 1 liter of methyl alcohol, and dried under vacuum at 60°C. There was obtained 375.7 g. of all-trans-β-apo-8'-carotenal; m.p. 138°C.

EXAMPLE 2

The Isomerization of β-Carotene 500 g. of crude, wet β-carotene, which contained both cis-isomers and the all-trans-isomer and which had a solids content of 44.2% (127.9 g. of which was β-carotene) and $E_{1\ cm}^{1\%} = 1329$ at 450 mμ (determined on a dry sample), produced in accordance with Example 1 of U.S. Patent 3,441,623, was placed in a flask with 2.5 liters of water. The contents of the flask were stirred at its boiling temperature for 20 hours under an atmosphere of nitrogen, until u.v. analysis and thin layer chromatography showed that substantially all the cis-isomers had been converted to the all-trans-isomer. The reaction was allowed to cool to room temperature, and the water was removed by decanting. One liter of acetone was added to the flask containing the carotene, and this was stirred for one hour at room temperature to disintegrate the lumps into fine red crystals. The product was filtered and washed with additional acetone on the filter and dried under vacuum at 60°C. There was obtained 133.9 g. of crude all-trans-β-carotene; $E_{1\ cm}^{1\%} = 2375$ at 454 mμ (cyclohexane). The absence of a second u.v. peak at 320 mμ showed that the material contained no cis-β-carotene. Recrystallization from heptane yielded pure trans-β-carotene.

I claim:

1. A process for converting a cis-isomer of a solid carotenoid to an all-trans-isomer of the carotenoid, comprising: immersing the cis-isomer in water and heating to a temperature of from about 50°C. to about 120°C.

2. The process of claim 1 wherein said carotenoid is a carotenoid hydrocarbon or a carotenoid containing one or more carbonyl groups.

3. The process of claim 2 wherein said cis-isomer is heated to a temperature of about 70°C. to about 100°C.

4. The process of claim 3 wherein said cis-isomer is heated to a temperature of about 100°C.

5. The process of claim 1 wherein said carotenoid contains one or more carbonyl groups.

6. The process of claim 1 wherein said carotenoid is β-apo-8'-carotenal.

7. The process of claim 1 wherein said carotenoid is a hydrocarbon.

8. The process of claim 7 wherein said carotenoid is β-carotene.

* * * * *